US007011652B1

(12) United States Patent

Berke et al.

(10) Patent No.: US 7,011,652 B1
(45) Date of Patent: Mar. 14, 2006

(54) EYE WASH STATION

(75) Inventors: Joseph J. Berke, West Bloomfield, MI (US); Charles T. Michael, Troy, MI (US); Alex Rhodes, West Bloomfield, MI (US)

(73) Assignee: Berke-Tec, Inc., Detroit, MI (US)

( * ) Notice: Subject to any disclaimer, the term of this patent is extended or adjusted under 35 U.S.C. 154(b) by 426 days.

(21) Appl. No.: 10/321,684

(22) Filed: Dec. 18, 2002

(51) Int. Cl.
*A61M 35/00* (2006.01)
*A61H 33/00* (2006.01)

(52) U.S. Cl. ........................... 604/300; 604/302; 4/620

(58) Field of Classification Search ........ 604/294–302; 239/99; 4/620, 624
See application file for complete search history.

(56) References Cited

U.S. PATENT DOCUMENTS 4,012,798 A 3/1977 Liautaud
4,493,119 A * 1/1985 Baumann ........................ 4/620
5,030,214 A * 7/1991 Spector ....................... 604/301
5,133,702 A * 7/1992 Py ............................. 604/302
5,216,765 A * 6/1993 Paterson et al. ............... 4/620
5,508,283 A 4/1996 Eicken et al.
5,695,124 A 12/1997 Demeny et al.
5,850,641 A 12/1998 Demeny et al.
6,296,626 B1 10/2001 Stein
6,336,917 B1 1/2002 Berke
6,398,766 B1 6/2002 Branch
6,444,692 B1 9/2002 Schelberger et al.
6,569,131 B1 * 5/2003 Michael et al. ............. 604/295

* cited by examiner

*Primary Examiner*—Tatyana Zalukaeva
*Assistant Examiner*—C. Lynne Anderson
(74) *Attorney, Agent, or Firm*—Alex Rhodes

(57) ABSTRACT

An eye wash station for administering an eye wash fluid to an eye which has been exposed to a noxious gas, or solid or liquid which can irritate or injure said eye. In a first aspect of the invention, a flexible bag, filled with an eye wash fluid is suspended from a hook or a stand. The flexible bag is operatively connected with a flexible tube to an applicator which is fed by gravity from the bag. The applicator includes a retractor for opening and holding open the eyelids of the eye which is being treated and a valve for controlling the amount of eye wash fluid which is applied to the eye. In second and third aspects of the invention, the applicator is connected with a pressurized water supply. One benefit if the invention is that it is disposable. Another benefit of the first and second aspects is that they are portable.

32 Claims, 5 Drawing Sheets

60
59
58

57

50
51
54
55
52
53
56

58
59
60
51
57
7
7

EYE WASH STATION

FIELD OF THE INVENTION

This invention relates to eye wash stations and more particularly to an eye wash station for applying eye wash liquids to eyes which have been exposed to gaseous fumes, or solid or liquid materials which irritate and/or injure eyes.

BACKGROUND OF THE INVENTION

Eye wash stations and fountains are used in hospitals and other facilities to treat eyes which have been exposed to gaseous fumes, or solid or liquid materials, such as chlorinated solvents, acids and bases that irritate and/or injure eyes. The Federal Occupational Safety and Health Administration (OSHA) has made eye wash stations mandatory in certain industrial facilities. One drawback with existing stations is that they require periodic maintenance to insure availability of non-contaminated eye wash fluids. Another drawback of many stations is that they are costly to purchase and costly to install. Another drawback is inadequate control over the discharge of eye wash fluids.

Another drawback is that there are no provisions in eye wash stations for preventing or controlling a natural tendency of eyelids to blink or close when eye wash fluids are sprayed on to eyes. Berke U.S. Pat. No. 6,336,917 and Berke et al. U.S. application Ser. No. 10/266,154 disclose eyelid retractors in which eyelids are opened and held open by applying a light pressure against upper and lower eyelids. Excessive pressure on eyes is prevented by limiting the intrusion of the retractor into the eyes. Another drawback is that under the current practice, outdoor workers whose eyes had been exposed to harmful materials must be transported to facilities where eye wash stations are available.

SUMMARY OF THE INVENTION

The present invention overcomes all of the foregoing drawbacks. It is a primary object of the present invention to provide an eye wash station for medical facilities and workplaces which provides immediate and effective relief to eyes which have been exposed to materials which can irritate or injure eyes. It is another object to provide a moderately priced eye wash station which is easy to install. It is another object to provide a disposable eye wash station. It is another object to provide a portable eye wash station which can be used by physicians and emergency personnel in the field.

With the foregoing objects in mind, in a first aspect of the invention, an improved eye wash station comprises a flexible reservoir; an eye wash fluid in the interior of the reservoir; a gravity fed applicator, preferably having an eyelid retractor and a valve for manually discharging an eye wash fluid; a flexible tube for connecting the reservoir with the applicator; and a means for suspending the reservoir. In a second aspect of the invention, the applicator of the first aspect is connected to a faucet of a sink. In a third aspect, the applicator is connected to a distribution system of a facility water supply.

In employing the teaching of the present invention, a plurality of alternate constructions can be provided to achieve the desired results and capabilities. In this disclosure, some alternate constructions are discussed. However, these embodiments are intended as examples, and should not be considered as limiting.

Further objects, benefits and characterizing features of the invention will become apparent from the ensuing detailed description and drawings which illustrate and describe the invention. The best mode which is contemplated in practicing the invention together with the manner of using the invention are disclosed and the property in which exclusive rights are claimed is set forth in each of a series of numbered claims at the conclusion of the detailed description.

BRIEF DESCRIPTION OF THE DRAWINGS

The invention will be better understood and further objects, characterizing features, details and advantages thereof will appear more clearly with reference to the diagrammatic drawings illustrating a presently preferred specific embodiment of the invention by way of non-limiting example only.

DETAILED DESCRIPTION OF A PREFERRED EMBODIMENT

Figure 3:
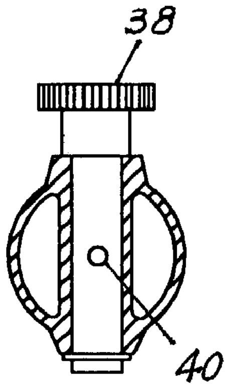
FIG. 3 is a cross-sectional view taken on the line 3—3 in FIG. 2.
Figure 1:
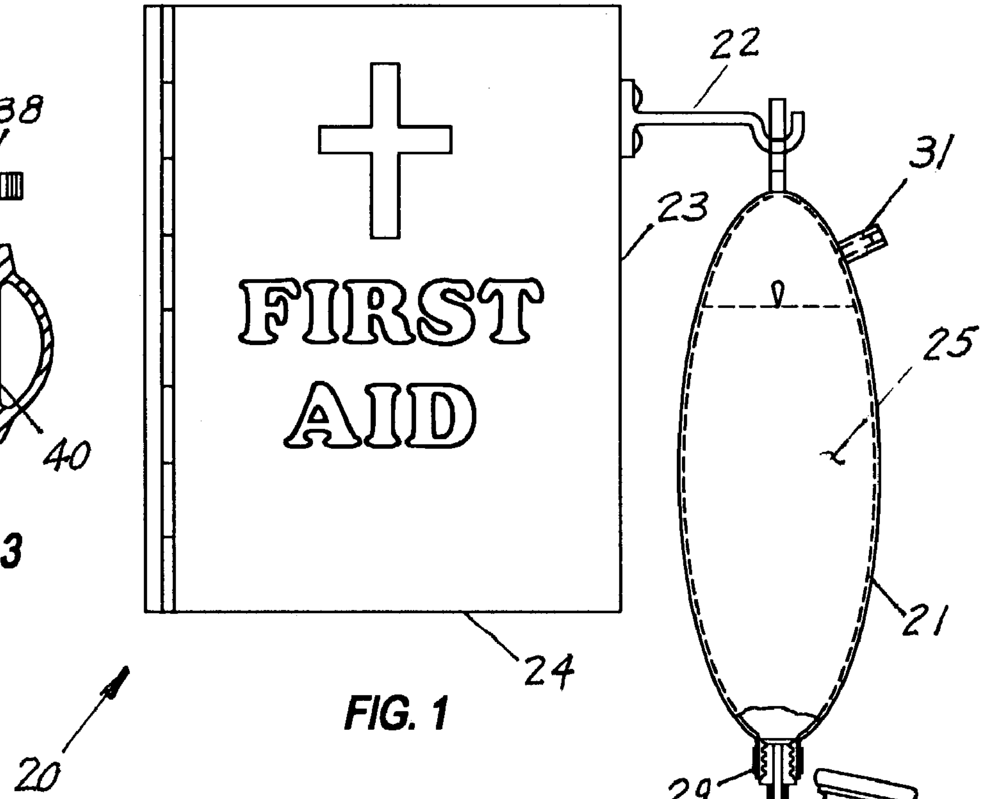
FIG. 1 is a front view of a first aspect of an eye wash station according to the present invention.
Figure 1:
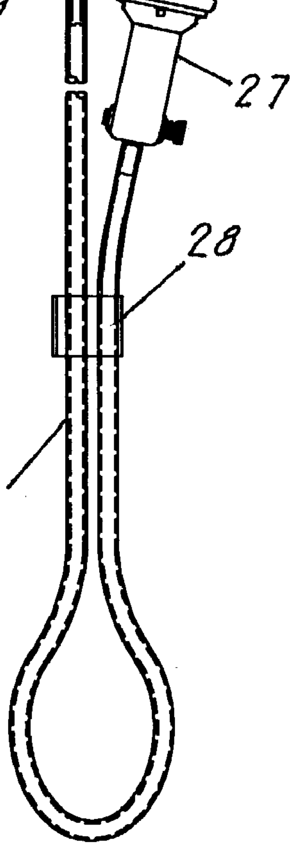
Figure 2:
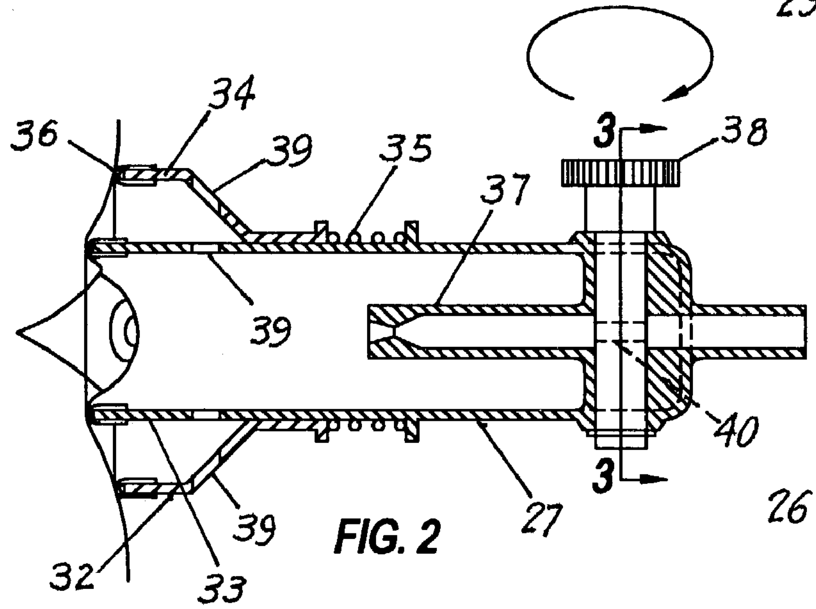
FIG. 2 is an enlarged longitudinal cross-sectional view through an applicator of the eye wash station.
Figures 4, 5, 6, 7:
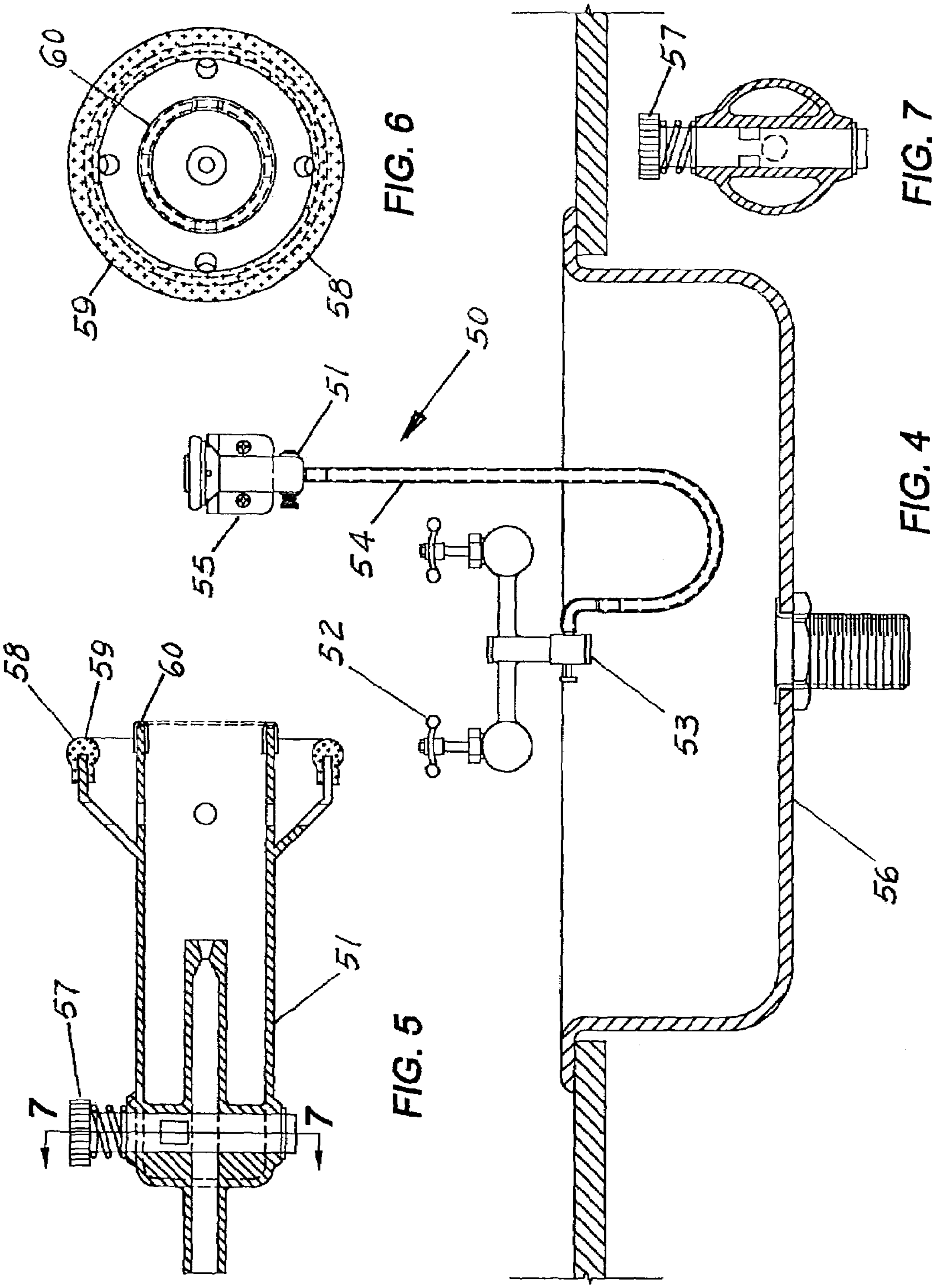
FIG. 4 is a front view of a second aspect of the present invention.
FIG. 5 is an enlarged longitudinal cross-sectional view through an applicator of the second aspect of the eye wash station.
FIG. 6 is an end view of the applicator.
FIG. 7 is a cross-sectional view taken on the line 7—7 in FIG. 5.
Figure 8:
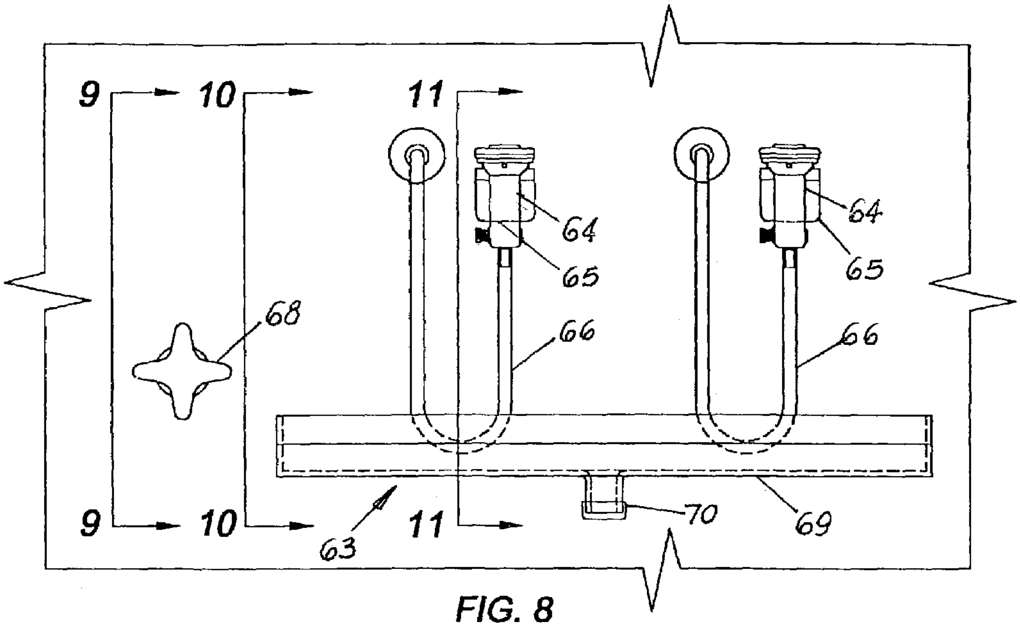
FIG. 8 is a front view of a third aspect of the present invention.
Figure 9:
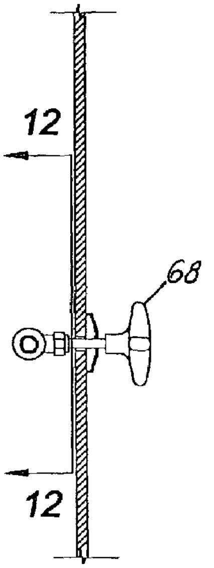
FIG. 9 is a cross-sectional view taken on the line 9—9 in FIG. 8.
Figure 10:
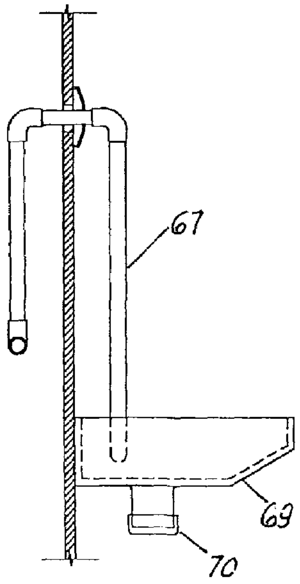
FIG. 10 is a cross-sectional view taken on the line 10—10 in FIG. 8.
Figure 11:
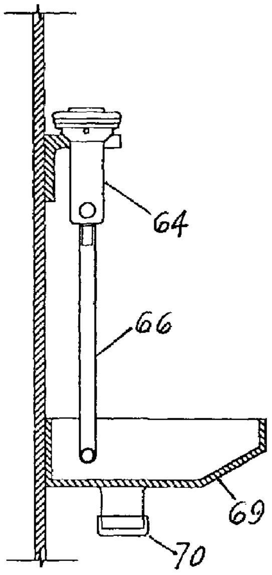
FIG. 11 is a cross-sectional view taken on the line 11—11 in FIG. 8.
Figure 12:
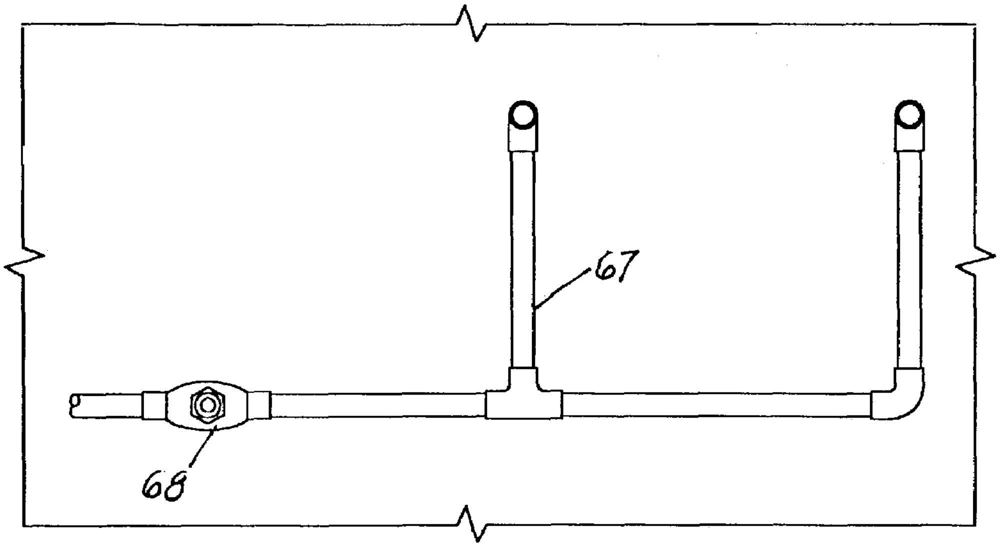
FIG. 12 is a cross-sectional view taken on the line 12—12 in FIG. 9.

Referring now to the drawings wherein like numerals designate like and corresponding parts throughout the several views, a first aspect of an eye wash station 20 is illustrated in FIGS. 1 through 3, according to the present invention. One distinguishing characteristic of this aspect is that it is independent of electrical power and water pressure. Another distinguishing feature is that it is portable. One benefit of this aspect is that it can be stored in a germ free package and quickly removed and assembled when a need arises. Another benefit is that it can be carried in the field by physicians and paramedics and immediately placed in service when a need arises.

The eye wash station 10 comprises a gravity feeding fluid reservoir 21 suspended from a wire hook 22, or by some other suitable means, such as an IV (intra venous) stand of a hospital. If these types of means for suspending the reservoir 21 are unavailable, the reservoir 21 can be manually suspended when the eye wash station 20 is in service. The reservoir 21 may be a flexible or rigid reservoir. The hook 22 shown in FIG. 1 is attached to a side wall 23 of a “First Aid” cabinet 24.

An eye wash fluid 25 is stored in the interior of the reservoir 21. A flexible tube 26 connects the reservoir 21 to a gravity fed applicator 27. A clip 28 on the flexible tube 26 retains the tube 26 as shown in FIG. 1.

Another feature of the eye wash station 20 is that it is disposable. Another feature is that it is moderate in price. Another feature is that it is easy to install. One benefit is that an eye wash fluid 25 may be applied at room temperature.

The reservoir 21 of FIG. 1 is a gravity feeding flexible bag, similar to the fixed or moveable type of bag used for administering IV solutions to hospital patients. The reservoir 21 can be quickly re-filled or replaced if additional eye wash fluid 25 is required. At an outlet end of the reservoir 21 there is a threaded closure 29 or some other usual means for filling the reservoir and operatively connecting the flexible tube 26. The reservoir 21 is connected to the flexible tube 26 engaging a tubular end portion of the closure 29 with the flexible tube 26.

In a side portion of the reservoir 21 there is a port 31 for injecting an antibiotic or some other enhancing agent, such as agents for purifying water and agents for destroying bacteria and microbial pathogens into the eye wash fluid 25. The reservoir 21, applicator 27 and flexible tube 26 are supplied in one or more sterile packages (not shown).

As an alternative to providing the eye wash station 20 pre-assembled and ready for immediate use, the eye wash station 20 can be provided in sterile packages in disassembled form. Before it is placed in service, it can be quickly assembled and suspended as shown in FIG. 1. The front end portion 32 of the applicator 27 which contacts the person is preferably covered with a usual type closure (not shown) to prevent contamination of the applicator before the applicator is placed in service. The means for retracting the eyelids is fully disclosed in Berke et al. U.S. application Ser. No. 10/266,154.

The construction of the applicator 27 is best understood by reference to FIG. 2. The applicator 27 is comprised of a cylindrical peri-ocular housing 33, a peri-orbital housing 34 slidably mounted on the peri-ocular housing 33 and a wire spring 35 which biases the peri-orbital housing 34 in a forward direction. The slidable peri-orbital portion 34 compensates for anatomical differences in individuals and limits the maximum pressure which can be exerted on a person’s eyelids.

The peri-ocular housing 33 includes a circular front edge portion 36 for contacting a person’s eyelids, a nozzle portion 37 for spraying the eye wash fluid 25 on to the person’s eye, and a rotary valve 38 for operatively connecting the reservoir 21 with the applicator 27. Drain holes 39 in the peri-ocular housing 33 and peri-orbital housing 34 allow the eye wash fluid 25 to circulate through the applicator 27. Before the eye wash station 20 is used, the rotary valve 38 is in a closed condition as shown in FIGS. 2 and 3. When the applicator 27 is placed in service, the rotary valve 38 is rotated 90 degrees to align an aperture 40 with the nozzle portion 37 of the applicator 27. The invention is used in the following manner.

When a need arises, if the eye wash station 20 is stored in disassembled form, if required, the reservoir 21 is filled with the eye wash fluid 25 and suspended as shown in FIG. 1. The applicator 27 is connected to one end of the flexible tube 26 and the other end of the tube 26 is connected to the outlet of the reservoir 21. The applicator 27 is grasped by an injured person and placed against his face with the peri-ocular portion 33 centered inside of his eye socket and the peri-orbital portion 34 bearing on the skeletal portion which surrounds the person’s eye. The applicator 27 is pressed forward to retract the person’s eyelids by advancing the peri-ocular portion 33 into the eye socket, the maximum amount of pressure on the eyelids being limited by the solid height of the spring 35. The rotary valve 38 is rotated to begin spraying the eye wash fluid 25 on to the affected eye. The amount of spray is governed by the amount of rotation of the valve 38.

With reference to FIGS. 4 through 7, inclusive, in a second aspect 50 of the invention an applicator 51 is connected to a conventional sink faucet 52 with a usual diverter valve 53 and a flexible tube 54. The applicator 51 is mounted on a wall bracket 55 above a sink 56. The applicator 51 of this embodiment is designated as a “retractor” in the co-pending Berke et al. U.S. patent application Ser. No. 10/266,154, which is incorporated herein, by reference. The faucet 52 and diverter valve 53 are preferably in an eyewash ready condition with the faucet 52 and diverter valve 53 set to allow water 25 to enter the flexible tube 54.

The applicator 51 has a valve 57 which is a resiliently biased, normally closed valve rather than the rotary valve 38 of the first described aspect. Another difference over the applicator 27 of the first aspect 20 is a fixed peri-orbital portion 58 with a soft resilient pad 59. The peri-ocular portion 60 and peri-orbital portion 58 are best understood by reference to FIGS. 5 and 6.

When a need to use the second aspect 50 arises, the applicator 51 is pressed against an injured eye to compress the soft resilient pad 59 and allow the peri-ocular portion 60 to enter a person’s eye socket. The resiliently biased valve 57 is then depressed to spray water 25 on to the person’s eye.

In FIGS. 8 through 12, inclusive, a third aspect 63 of the invention is disclosed wherein a pair of applicators 64, such as the applicators of the first 20 and second 50 aspects, are supported on wall brackets 65 and connected with flexible tubes 66 to pipes 67 of an existing water system. A valve 68 is provided at the inlet side of the water supply to shut down the eye wash station 63 in the event of a leaky tube or valve. A wall mounted catch basin 69 is provided below the applicators 64 to catch discharges of the eye wash fluid 25 from the applicators 64. A drain 70 is provided at the bottom of the basin 69 for draining water 25 from the basin 69. One benefit of this aspect 63 is that multiple applicators 64 can be easily provided in an eye wash station 63. One drawback is that modifications to a building and water system, though few, are required.

Figure 13:
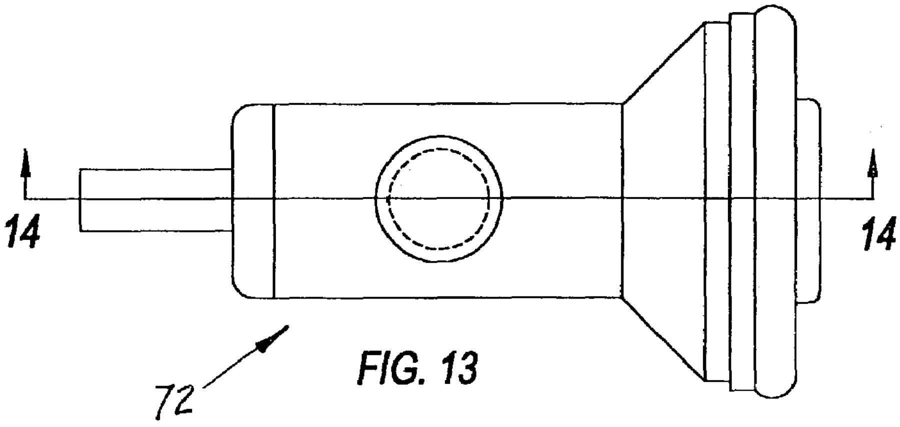
FIG. 13 is a plan view of an alternate embodiment of an applicator of an eye wash station.
Figure 14:
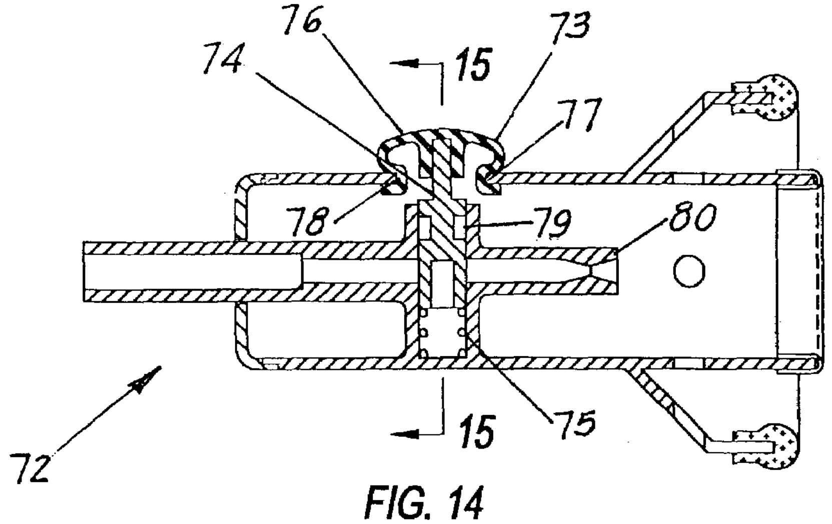
FIG. 14 is a longitudinal cross-sectional view through the applicator of FIG. 13.
Figure 15:
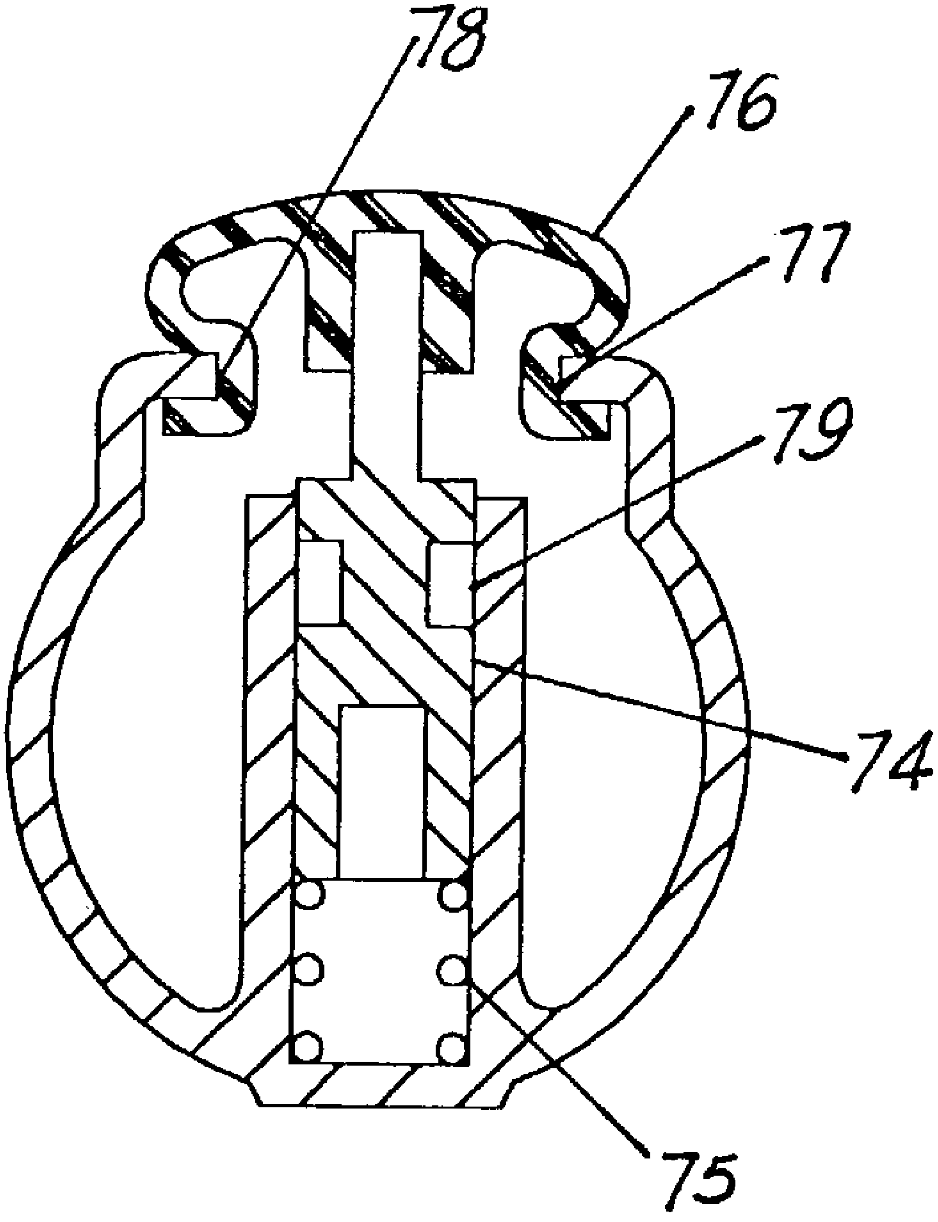
FIG. 15 is an enlarged longitudinal cross-sectional view taken on the line 15—15 in FIG. 14.

In FIGS. 13 through 15, inclusive, an alternate embodiment 72 of the applicators heretofore described is shown. The object of this embodiment 72 is to provide an applicator 72 which is more suitable for a single hand operation. The applicator 72 has a resiliently biased valve 73 comprised of a slidable valve body 74, a coil spring 75 and a flexible member 76 for depressing the valve body 74. The flexible member 76 is retained in a housing by engaging a groove 77 with an aperture 78 of the applicator 72. A spray of an eye wash fluid 25 is initiated by grasping the applicator 72 with the fingers and palm of a hand and closing the hand to depress the flexible member 76. When the flexible member 76 is depressed, a by-pass portion 79 of the valve body 74 is aligned with a nozzle 80 to permit the eye wash fluid 25 to enter the nozzle 80.

From the foregoing, it will be understood that our eye wash station has a number of important advantages over the prior art. One important advantage is that it requires little, if any, maintenance since it is disposable. Another important advantage is that it can be immediately placed in service. Still yet another important advantage is that it is easy to install at single, multiple or remote locations. Still yet another important advantage is that it provides a means for overcoming the tendency of eyelids to blink or close when they are struck by an eye wash fluid. Still yet another important advantage is that it is portable.

Although only several aspects of our invention have been illustrated and described, it is not our intention to limit the scope of our invention to these aspects since other embodiments can be derived by such obvious changes as changes in shape, size, arrangement of parts, elimination of parts, combining of parts, and substitution of parts within the spirit of our invention and the scope of the claims which are appended hereto.

We claim:

1. An eye wash station for administering an eye wash fluid to an eye which has been exposed to a noxious gas, or solid or liquid which can irritate or injure said eye comprising: a source for supplying an eye wash fluid; an eye wash fluid; an applicator for applying said eye wash fluid to said eye at a location which is remote from said source, said applicator having a means for retracting an eyelid; and a flexible tube for operatively connecting said applicator to said source of said eye wash fluid.

2. The eye wash station recited in claim 1 wherein said source for supplying said eye wash fluid is positioned above said applicator for gravity feeding said eye wash fluid to said applicator.

3. The eye wash station recited in claim 1 wherein said source for supplying said eye wash fluid is a suspended source of said eye wash fluid.

4. The eye wash station recited in claim 1 wherein said eye wash station is a disposable eye wash station.

5. The eye wash station recited in claim 1 wherein said source for supplying said eye wash fluid is a suspended eye wash fluid reservoir.

6. The eye wash station recited in claim 4 wherein said suspended reservoir is a replaceable reservoir.

7. The eye wash station recited in claim 5 wherein said suspended reservoir is a disposable reservoir.

8. The eye wash station recited in claim 5 wherein said suspended reservoir is a flexible bag.

9. The eye wash station recited in claim 5 further comprising a port for injecting an enhancing agent into said eye wash fluid.

10. The eye wash station recited in claim 1 wherein said source for supplying said eye wash fluid is a building water supply.

11. The eye wash station recited in claim 1 wherein said source for supplying said eye wash fluid is a faucet of a sink.

12. The eye wash station recited in claim 1 further comprising a valve for selectively adjusting an amount of said eye wash fluid which is applied to said eye.

13. The eye wash station recited in claim 12 wherein said valve is a rotary valve.

14. The eye wash station recited in claim 12 wherein said valve is a resiliently biased normally closed valve.

15. The eye wash station recited in claim 1 wherein said applicator includes a nozzle for spraying said eye wash fluid on to said eye.

16. The eye wash station recited in claim 1 further comprising a means for retracting an eyelid, said means comprises a portion of said applicator for applying pressure to said eyelid and a means for limiting said pressure on said eyelid.

17. The eyewash station recited in claim 16 wherein said means for limiting said pressure on said eyelids comprises a portion of said applicator for contacting a bony structure surrounding said eye.

18. The eyewash station recited in claim 16 further comprising a soft resilient pad on said portion of said applicator for limiting said pressure on said eyelid.

19. The eyewash station recited in claim 16 further comprising a spring between said eye retracting portion and said pressure limiting portion of said applicator.

20. A portable eye wash station for administering an eye wash fluid to an eye which has been exposed to a noxious gas, or solid or liquid which can irritate or injure said eye comprising: a suspended source of an eye wash fluid; an eye wash fluid, said source having a port for injecting an antibiotic or other enhancing agent; an applicator for applying said eye wash fluid to said eye, said applicator being remote from eye wash fluid source and having a valve for controlling the amount of said eye wash fluid which is administered to said eye; and a flexible tube for operatively connecting said applicator to said source of said eye wash fluid.

21. The portable eye wash station recited in claim 20 wherein said suspended source of said eye wash fluid is suspended from a movable stand.

22. The portable eye wash station recited in claim 20 wherein said suspended source of said eye wash fluid is a disposable flexible bag.

23. The portable eye wash station recited in claim 20 wherein said applicator comprises a means for retracting eyelids.

24. A disposable eye wash station for administering an eye wash fluid to an eye which has been exposed to a noxious gas, or solid or liquid which can irritate or injure said eye comprising: a suspended disposable reservoir for storing an eye wash fluid, an eye wash fluid stored in said reservoir; a disposable applicator connected to said reservoir for applying said eye wash fluid to said eye; and a disposable flexible tube for operatively connecting said applicator to said reservoir.

25. The disposable eye wash station recited in claim 24 further comprising a means for controlling a flow of said eye wash station from said flexible bag to said applicator.

26. The disposable eye wash station recited in claim 24 wherein said reservoir is replaceable.

27. The disposable eye wash station recited in claim 24 wherein said reservoir is refillable.

28. A method for administering an eye wash fluid to an eye which has been exposed to a noxious gas, or solid or liquid which can irritate or injure said eye, comprising the steps of: filling a reservoir with an eye wash fluid; suspending said reservoir above said eye; delivering a portion of said fluid in said reservoir by gravity to an inlet portion of an applicator which is remote from said reservoir; opening a valve to admit said eye wash fluid into said applicator and spraying said portion of said fluid with said applicator on to said eye.

29. The method for administering an eye wash fluid recited in claim 28 further comprising the step of retracting an eyelid with said applicator before said fluid is sprayed on to said eye.

30. The method for administering an eye wash fluid recited in claim 28 further comprising the step of regulating said spray of said fluid by partially opening and closing said valve.

31. The method recited in claim 28 further comprising the step of refilling said reservoir.

32. A method for administering an eye wash fluid to an eye which has been exposed to a noxious gas, or solid or liquid which can irritate or injure said eye, comprising the steps of: connecting an adapter to an outlet of a faucet; connecting a flexible hose of an eye wash station to said adapter; opening said faucet to allow water to flow from said faucet into said eye wash station; retracting an eyelid of said eye with an applicator of said eye wash station; opening a valve of said applicator to spray water on to said eye.

* * * * *